United States Patent [19]

Rolski et al.

[11] Patent Number: 4,558,053

[45] Date of Patent: Dec. 10, 1985

[54] NAPHTHALENE-1,5-DISULFONATE SALTS OF DIMERIC INDOLE-DIHYDROINDOLE ALKALOIDS

[75] Inventors: Stanislaw Rolski; Ralph R. Pfeiffer, both of Indianapolis, Ind.

[73] Assignee: Eli Lilly and Company, Indianapolis, Ind.

[21] Appl. No.: 564,119

[22] Filed: Dec. 21, 1983

[51] Int. Cl.$^4$ .................. A61K 31/475; C07D 519/04
[52] U.S. Cl. .................... 514/283; 260/244.4
[58] Field of Search ..................... 260/244.4; 424/262; 514/283

[56] References Cited

U.S. PATENT DOCUMENTS

| Re. 30,560 | 3/1981 | Miller et al. | 260/244.4 |
| 3,097,137 | 9/1963 | Beer et al. | 424/262 |
| 3,205,220 | 9/1965 | Svoboda et al. | 424/262 |
| 4,012,390 | 3/1977 | Cullinan | 260/244.4 |
| 4,143,041 | 3/1979 | Thompson | 260/244.4 |
| 4,191,688 | 3/1980 | Conrad et al. | 260/244.4 |
| 4,259,242 | 3/1981 | Rolski | 260/244.4 |

Primary Examiner—Donald G. Daus
Assistant Examiner—Diana G. Rivers
Attorney, Agent, or Firm—James L. Rowe; Arthur R. Whale

[57] ABSTRACT

Stable, biologically available, orally active 1,5-naphthalenedisulfonate salt of vinzolidine.

8 Claims, No Drawings

NAPHTHALENE-1,5-DISULFONATE SALTS OF DIMERIC INDOLE-DIHYDROINDOLE ALKALOIDS

BACKGROUND OF THE INVENTION

A number of indole-dihydroindole alkaloids are currently either being marketed or are or have been on clinical trial as anticancer agents. These alkaloids include vincaleucoblastine (vinblastine, VLB)—marketed as VELBAN, U.S. Pat. No. 3,097,137; vincristine (VCR, leurocristine)—marketed as ONCOVIN, U.S. Pat. No. 3,205,220; vindesine (VDS)—marketed as ELDISINE, U.S. Pat. No. 4,191,688; vinzolidine, U.S. Pat. No. Re. 30,560; and vinepidine, U.S. Pat. No. 4,143,041. A large number of acid addition salts of these drugs are disclosed, including the naphthalene-1-sulfonate and the naphthalene-2-sulfonate.

In general, the sulfate salts of the above dimeric indole-dihydroindole alkaloids are favored during isolation, synthesis, formulation, etc. The drugs are customarily administered parenterally by the iv route and any pharmaceutically-acceptable soluble salt, such as the sulfate, which can provide the required concentration of drug, can be used. Sulfate salts of VLB and vincristine are prepared by neutralization of the base with dilute sulfuric acid (ethanol for example or other inert polar solvent may also be present to solubilize the base) followed by lyophilization. With these alkaloids, the lyophilized salt had adequate stability, but with vindesine, the lyophilized salt was not stable. Rolski, U.S. Pat. No. 4,259,242 addresses this problem and provides a method of preparing a stable monosulfate salt of vindesine by precipitation during neutralization of vindesine base with sulfuric acid in acetonitrile solution.

Vinzolidine is another indole-dihydroindole alkaloid whose sulfate salt has been found to be unstable. In contrast to the other alkaloids, vinzolidine is an orally active drug and must be capable of being provided in solid formulations such as capsules and tablets. While an injectable product like vindesine or vincristine can be lyophilized and the lyophilized product sealed in a dry, inert atmosphere, capsules and tablets are constantly exposed to air and water vapor.

Vinzolidine sulfate was prepared in eight different crystalline forms by employing different recrystallization solvents. While the stability of these forms varied considerably, none was found to be sufficiently stable to meet the stability requirements of an oral dosage form.

It is an object of this invention to prepare a vinzolidine salt which is sufficiently stable for use in oral dosage forms and which furnishes adequate vinzolidine blood levels on ingestion.

SUMMARY OF THE INVENTION

In fulfillment of the above and other objects, this invention provides 1,5-naphthalene disulfonate salts of indole-dihydroindole alkaloids of the formula

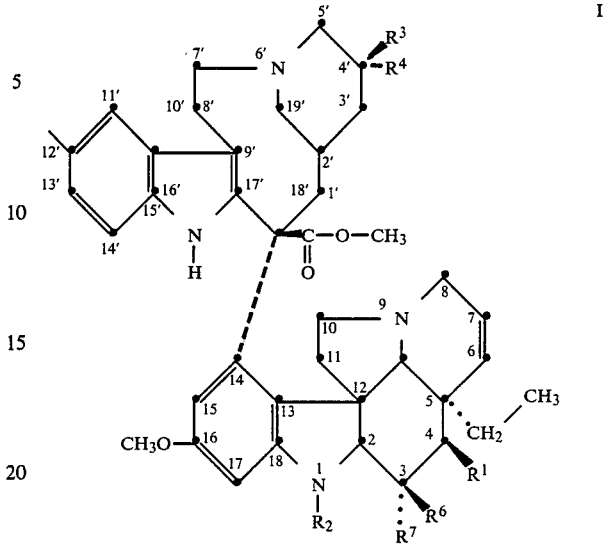

wherein is OH or O—CO—CH$_3$, R$^2$ is CH$_3$ or CHO; one of R$^3$ and R$^4$ is ethyl and the other is OH; when taken singly, R$^6$ is OH and R$^7$ is CO—OCH$_3$ or CO—R$^9$, wherein R$^9$ is NH$_2$, NH—C$_{1-3}$ alkyl-X, wherein X is hydrogen, chloro or bromo, or C$_{1-3}$ loweralkanoyloxy; when R$^6$ and R$^7$ are taken together with the carbon atoms to which they are attached, they form a spiro-oxazolidinedione ring permissibly substituted at N$_3''$ with C$_{1-3}$ alkyl or chloro-substituted C$_{1-3}$ alkyl.

In the above formula, where R$^1$ is acetoxy, R$^2$ is methyl, R$^6$ is OH, R$^7$ is CO—OH$_3$, R$^3$ is hydroxyl and R$^4$ is ethyl, VLB (vincaleucoblastine, vinblastine) is represented; where R$^1$ is acetoxy, R$^2$ is formyl, R$^6$ is OH, R$^7$ is CO—OCH$_3$, R$^3$ is hydroxyl and R$^4$ is ethyl, vincristine (leurocristine, VCR) is represented; where R$^1$ is acetoxy, R$^2$ is methyl, R$^6$ is OH, R$^7$ is CO—OCH$_3$, R$^3$ is ethyl and R$^4$ is hydroxyl, leurosidine (vinrosidine) is represented; where R$^6$ and R$^7$, together with the carbon to which they are attached, form an oxazolidindione ring with a chloroethyl group at N$_3''$, R$^2$ is CH$_3$, R$^1$ is acetoxy, R$^3$ is OH and R$^4$ is ethyl, vinzolidine is represented; and when R$^2$ is CH$_3$, R$^3$, R$^6$ and R$^1$ are OH, R$^4$ is ethyl, R$^7$ is COR$^9$ and R$^9$ is NH$_2$, vindesine is represented.

The preparation of vinzolidine 1,5-naphthalene disulfonate is illustrated below.

EXAMPLE 1

Preparation of vinzolidine 1,5-naphthalenedisulfonate

To 1% (w/v) solution of vinzolidine free base (95+% purity) in methanol is added dropwise with stirring a stoichiometric amount (1 mole per mole) of a 2% methanolic solution of 1,5-naphthalenedisulfonic acid. The resulting solution was allowed to stand at ambient temperature for about two hours, during which time period crystallization of the vinzolidine 1,5-naphthalenedisulfonate salt begins. The crystallizing solution is kept at about 0° C. overnight and is then filtered. The filter cake is washed with a small amount of methanol and then dried in vacuo overnight at ambient temperature. The salt is then allowed to stand in air for about two hours. The yield of vinzolidine 1,5-naphthalenedisulfonate is 95–97%.

EXAMPLE 2

Alternate Preparation of Vinzolidine 1,5-Naphthalene Disulfonate in Three Steps a. Conversion of vinzolidine free base to vinzolidine sulfate

To a 1% solution of free base in anhydrous ethanol, a stoichiometric amount of 1.0N sulfuric acid is added in dropwise fashion with stirring [1.0 g. of free base (~93% purity) requires ~2 ml. of 1.0N sulfuric acid]. Stirring is continued until some opalescence appears. The solution is allowed to stand at room temperature for two additional hours followed by 2-3 hours at about 0° C. The precipitate is then filtered on a sintered glass funnel, washed with a small amount of anhydrous ethanol and dried in vacuo at 45°; yield = ~85%. Additional salt (ca. 10%) can be obtained from the filtrate.

This sulfate salt contains ca. 9% of water (possibly in the form of a pentahydrate). A sharp X-ray pattern was obtained.

b. Preparation of amorphous vinzolidine 1,5-naphthalenedisulfonate

A 10% aqueous solution of 1,5-naphthalenedisulfonic acid disodium salt is added dropwise with stirring to a 2% aqueous solution of vinzolidine sulfate. A 10% excess of 1,5-naphthalenedisulfonic acid disodium salt is used; i.e., 1.1 mole of acid per mole of base. After holding the mixture at about 0° C. overnight, the precipitate is filtered on a sintered glass funnel, washed with a small amount of water, and dried in vacuo overnight at room temperature. An amorphous material is obtained that contains ~7% of $H_2O$ (yield = >80 percent).

c. Crystallization of amorphous material

The amorphous material is added gradually to methanol with stirring (1 g. per 100 ml. of methanol). After the addition is complete, the suspension is stored in the refrigerator overnight. Subsequent handling is the same as in Example 1. The salt crystallizes as a methanolate (Form I) by both methods and contains three molecules of methanol per molecule of salt.

Vacuum drying removes the methanol but equilibration of the desired salt in air gives a hydrate (Form II); Karl Fisher ~8% water. Form II dissolves to the extent of about 150 mcg./ml. in water at 25° C.

A third crystalline form, Form III, is produced by recrystallizing the salt in boiling methanol and then drying the methanolate in air, which procedure yields a different hydrate containing about 6% water. The X-ray diffraction patterns of these three forms follow. The patterns were obtained using an X-ray tube with a copper target and a nickel filter.

| FORM I | |
|---|---|
| d | $I/I_1$ |
| 12.15 | .80 |
| 10.88 | .16 |
| 9.80 | 1.00 |
| 8.14 | .16 |
| 7.58 | .28 |
| 7.24 | .20 |
| 6.52 | .64 |
| 6.18 | .16 |
| 5.90 | .04 |
| 5.55 | .16 |
| 4.89 | .44 |
| 4.57 | .36 |
| 4.42 | .44 |
| 4.17 | .40 |
| 3.97 | .32 |
| 3.76 | .64 |
| 3.56 | .40 |
| 3.34 | .44 |
| 3.26 | .24 |
| 3.08 | .04 |
| 2.95 | .04 |
| 2.89 | .04 |
| 2.77 | .04 |
| 2.67 | .04 |
| 2.54 | .04 |
| 2.46 | .04 |
| 2.40 | .04 |
| 2.28 | .04 |
| 2.22 | .04 |
| 2.15 | .04 |
| 2.08 | .06 |
| FORM II | |
| 12.65 | .14 |
| 10.54 | .48 |
| 9.47 | 1.00 |
| 7.98 | .07 |
| 7.32 | .17 |
| 7.15 | .59 |
| 6.69 | .21 |
| 6.11 | .17 |
| 5.44 | .41 |
| 5.14 | .31 |
| 4.71 | .52 |
| 4.50 | .10 |
| 4.36 | .28 |
| 4.16 | .14 |
| 4.07 | .14 |
| 3.92 | .07 |
| 3.78 | .14 |
| 3.57 | .07 |
| 3.47 | .28 |
| 3.34 | .17 |
| 3.23 | .07 |
| 3.13 | .07 |
| 3.03 | .03 |
| 2.91 | .03 |
| 2.79 | .03 |
| 2.68 | .03 |
| 2.60 | .02 |
| 2.49 | .03 |
| 2.38 | .02 |
| 2.32 | .02 |
| 2.25 | .03 |
| 2.22 | .02 |
| 2.17 | .02 |
| 2.12 | .02 |
| FORM III | |
| 10.85 | .55 |
| 10.16 | .05 |
| 9.26 | 1.00 |
| 7.41 | .05 |
| 6.76 | .55 |
| 6.28 | .80 |
| 5.68 | .20 |
| 5.40 | .20 |
| 5.07 | .10 |
| 4.75 | .40 |
| 4.33 | .30 |
| 4.20 | .15 |
| 4.00 | .20 |
| 3.75 | .05 |
| 3.42 | .15 |
| 3.30 | .05 |
| 3.15 | .08 |
| 3.02 | .05 |
| 2.92 | .08 |
| 2.82 | .05 |
| 2.69 | .05 |

Naphthalene-1,5-disulfonate salts were also prepared from vinblastine, vincristine and vindesine. The salts were stable, white solids sparingly soluble in water.

One of the above salts, the orally active vinzolidine 1,5-naphthalenedisulfonate, (vinzolidine napadisilate) is of particular interest since it is approximately bioequivalent to vinzolidine sulfate.

Dosage forms suitable for oral administration have more stringent requirements than do parenteral dosage forms; i.e., the drug must be stable when mixed with pharmaceutically-acceptable excipients customarily used in preparing solid dosage forms such as capsules or tablets. Any such modification of drug form must not substantially increase toxicity nor decrease oral efficacy.

The ability of vinzolidine 1,5-naphthalenedisulfonate to meet these requirements as an oral drug are set forth below.

In the first place, as regards stability, bulk vinzolidine 1,5-naphthalene disulfonate remained virtually unchanged at one year at the following storage temperatures—5° C.; 25° C.; 40° C. In addition, the bulk material was stable for one year at 40° C. and 75% relative humidity. Vinzolidine 1,5-naphthalene disulfonate-containing capsules had a potency of 94.3% of the initial potency after storage for one year at 40° C. and 75% relative humidity. Under the same storage conditions, both bulk and encapsulated vinzolidine sulfate were clearly less stable.

Secondly, as regards toxicity, the $LD_{50}$ in mice of vinzolidine 1,5-naphthalenedisulfonate is 68–7 mg./kg. compared to 37.7 mg./kg. for vinzolidine sulfate.

Thirdly, as regards oncolytic activity, the 1,5-disulfonate salt shows good antitumor activity against transplanted tumors in mice. For example, using the 1,5-naphthalenedisulfonate salt, against the 6C3HED lymphosarcoma, a single oral dose of 11 mg./kg. (in either acacia or empulphor suspension) gives about a 50% inhibition of tumor growth and single doses of 15–22.5 mg./kg. give 95–100% inhibition.

Finally, vinzolidine 1,5-naphthalenedisulfonate is well-absorbed when administered by the oral route. For example, when each of six monkeys was given a single capsule containing a 1.5 mg./kg. dose of vinzolidine base equivalent or about 2 mg./kg. of vinzolidine 1,5-naphthalenedisulfonate, excellent blood levels of vinzolidine were obtained. Table 1 which follows give pooled mean serum concentrations of the drug in mg./ml for the six monkeys at given time intervals with the standard deviation.

TABLE 1

| Time in Hours | Mean Serum Concentration Mg./Ml. ± SD |
| --- | --- |
| 1/12 | 0 |
| ½ | 0.46 ± 0.28 |
| 1 | 29.38 ± 7.80 |
| 4 | 19.53 ± 3.25 |
| 8 | 5.32 ± 0.93 |
| 24 | 0.66 ± 0.28 |
| 48 | 0.05 ± 0.04 |
| 72 | 0 |
| 96 | 0 |

The above serum concentrations are comparable to those obtained with vinzolidine sulfate orally.

Oral formulations of vinzolidine 1,5-naphthalenedisulfonate include telescoping gelatin capsules, tablets, suspensions and the like such that each capsule, tablet or unit of suspension (teaspoon) contains a single dosage unit of the drug. Such dosage unit will contain about 30 mgs. of vinzolidine base as the 1,5-naphthalenedisulfonate salt. 1,5-Naphthalenedisulfonate salts of other indole-dihydroindole alkaloids represented by I above can be formulated similarly.

We claim:

1. A 1,5-naphthalenedisulfonate salt of an indole-dihydroindole alkaloid of the formula

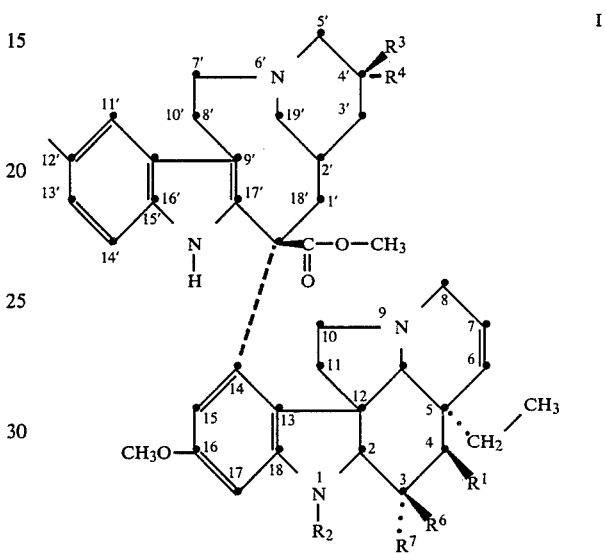

wherein $R^1$ is OH or O—CO—CH$_3$, $R^2$ is CH$_3$ or CHO; one of $R^3$ and $R^4$ is ethyl and the other is OH; when taken singly, $R^6$ is OH and $R^7$ is CO—OCH$_3$ or CO—R$^9$, wherein $R^9$ is NH$_2$, NH—C$_{1-3}$ alkyl-X, wherein X is hydrogen, chloro or bromo, or C$_{1-3}$ loweralkanoyloxy; when $R^6$ and $R^7$ are taken together with the carbon atoms to which they are attached, they form a spiro-oxazolidinedione ring permissibly substituted at N3″ with C$_{1-3}$ alkyl or chloro-substituted C$_{1-3}$ alkyl.

2. A compound according to claim 1, said compound being the 1,5-naphthalenedisulfonate salt of vinzolidine.

3. A compound according to claim 1, said compound being vincristine 1,5-naphthalenedisulfonate.

4. A compound according to claim 1, said compound being vinblastine 1,5-naphthalenedisulfonate.

5. A compound according to claim 1, said compound being vindesine 1,5-naphthalenedisulfonate.

6. A pharmaceutical formulation for oral administration in dosage unit form containing per dosage unit an oncolytic amount of vinzolidine 1,5-naphthalenedisulfonate plus an inert pharmaceutical excipient.

7. A polymorphic form of compound according to claim 2, said polymorphic form being vinzolidine 1,5-naphthalenedisulfonate Form II.

8. A polymorphic form of a compound according to claim 2, said polymorphic form being vinzolidine 1,5-naphthalenedisulfonate Form III.

* * * * *